US008082280B2

(12) United States Patent
Compton et al.

(10) Patent No.: US 8,082,280 B2
(45) Date of Patent: Dec. 20, 2011

(54) COMPUTERIZED METHOD AND SYSTEM FOR CODING-BASED NAVIGATION

(75) Inventors: David L. Compton, Lenexa, KS (US); James D. Eaton, Jr., Gardner, KS (US); Paula S. Matarrese, Kansas City, MO (US); Manikandan Nair, Olathe, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 295 days.

(21) Appl. No.: 10/977,983

(22) Filed: Oct. 29, 2004

(65) Prior Publication Data

US 2006/0106795 A1    May 18, 2006

(51) Int. Cl.
*G06F 17/30* (2006.01)

(52) U.S. Cl. ...................................... 707/805

(58) Field of Classification Search .................. None
See application file for complete search history.

(56) References Cited

U.S. PATENT DOCUMENTS

| | | | |
|---|---|---|---|
| 5,229,584 A | 7/1993 | Erickson | |
| 5,325,293 A | 6/1994 | Dorne | |
| 5,508,912 A * | 4/1996 | Schneiderman | 705/3 |
| 5,583,758 A | 12/1996 | McIlroy et al. | |
| 5,823,948 A * | 10/1998 | Ross et al. | 600/300 |
| 5,845,253 A | 12/1998 | Rensimer et al. | |
| 5,845,255 A * | 12/1998 | Mayaud | 705/3 |
| 5,715,449 A | 2/1999 | Peters, Jr. et al. | |
| 5,924,074 A | 7/1999 | Evans | |
| 5,963,952 A * | 10/1999 | Smith | 707/102 |
| 6,154,726 A | 11/2000 | Rensimer et al. | |
| 6,192,380 B1 * | 2/2001 | Light et al. | 715/505 |
| 6,212,519 B1 * | 4/2001 | Segal | 707/6 |
| 6,278,999 B1 * | 8/2001 | Knapp | 707/9 |
| 6,529,876 B1 * | 3/2003 | Dart et al. | 705/4 |
| 6,915,254 B1 * | 7/2005 | Heinze et al. | 704/9 |
| 6,981,001 B1 * | 12/2005 | Reddick et al. | 707/104.1 |
| 7,006,979 B1 * | 2/2006 | Samra et al. | 705/10 |
| 7,110,955 B1 * | 9/2006 | Barhnart et al. | 705/3 |
| 7,127,405 B1 * | 10/2006 | Frank et al. | 705/1 |
| 7,716,072 B1 * | 5/2010 | Green et al. | 705/3 |
| 2001/0039503 A1 * | 11/2001 | Chan et al. | 705/2 |
| 2002/0147615 A1 | 10/2002 | Doerr et al. | |
| 2003/0197735 A1 * | 10/2003 | Woltzen | 345/777 |
| 2004/0030586 A1 * | 2/2004 | Cucchiara et al. | 705/3 |
| 2004/0039710 A1 | 2/2004 | McMillan et al. | |

(Continued)

OTHER PUBLICATIONS

The T-SystemEV® EDIS—ED Information Systems—Coding, Transforming the ED Experience . . . , www.tsystem.com website, published Jul. 12, 2004.
Stat E&M CoderTM, Code with care: You're being watched—Medical Economics May 2004, www.statcoder.com website, published May 11, 2004.

(Continued)

*Primary Examiner* — Bai D. Vu
(74) *Attorney, Agent, or Firm* — Shook, Hardy & Bacon L.L.P.

(57) ABSTRACT

Computerized methods and systems for professional evaluation and management coding of a patient visit based upon documentation are provided. Such methods and systems increase efficiency and enhance the quality of clinician documentation by permitting automatic coding as a byproduct of documentation and eliminating the necessity for an after-the-fact check of the patient's chart to ensure appropriate documentation. Computerized methods and systems for navigating to a portion of an electronic record, e.g., an electronic medical record, based upon professional evaluation and management coding are also provided, as is the automatic insertion of document content where necessary.

14 Claims, 9 Drawing Sheets

U.S. PATENT DOCUMENTS

| | | | |
|---|---|---|---|
| 2004/0117206 A1* | 6/2004 | Steinberger et al. | 705/2 |
| 2004/0153338 A1* | 8/2004 | Kim et al. | 705/2 |
| 2004/0204961 A1 | 10/2004 | Rensimer et al. | |
| 2004/0254816 A1* | 12/2004 | Myers | 705/2 |
| 2005/0154615 A1* | 7/2005 | Rotter et al. | 705/3 |
| 2005/0177050 A1* | 8/2005 | Cohen | 600/509 |
| 2005/0222873 A1* | 10/2005 | Nephin et al. | 705/2 |
| 2005/0273363 A1* | 12/2005 | Lipscher et al. | 705/2 |
| 2006/0106648 A1* | 5/2006 | Esham et al. | 705/3 |

OTHER PUBLICATIONS

Reference #A—. . . WayBack Machine, Archive Date of: Feb. 2, 2003 (12 pages__).

Office Action, dated May 21, 2009 from U.S. Appl. No. 10/977,985, filed Oct. 29, 2004.

Final Office Action dated Mar. 24, 2010 for U.S. Appl. No. 10/977,985.

* cited by examiner

COMPUTERIZED METHOD AND SYSTEM FOR CODING-BASED NAVIGATION

CROSS-REFERENCE TO RELATED APPLICATIONS

This application is related by subject matter to the invention disclosed in the commonly assigned application U.S. application Ser. No. 10/977,985, entitled "Computerized Method and System for Documentation-Based Coding", which was filed on even date herewith.

STATEMENT REGARDING FEDERALLY SPONSORED RESEARCH OR DEVELOPMENT

Not applicable.

TECHNICAL FIELD

The present invention relates generally to the field of computer software. More particularly, the present invention relates to a computerized method and system for professional evaluation and management (E&M) coding of a patient visit, e.g., to a hospital or clinical Emergency Department, based upon documentation. The present invention further relates to a computerized method and system for navigating to a portion of an electronic record, e.g., an electronic medical record, based upon E&M coding.

BACKGROUND OF THE INVENTION

To ensure appropriate documentation for professional services rendered, e.g., in a hospital Emergency Department, clinicians are required to document particular elements based upon a patient's clinical presentation and the reason for the patient's visit. Based upon the quantity of documented elements within components and subcomponents particularly set forth in the CMS 95 Coding Guidelines for Professional Evaluation and Management (E&M) Coding, a patient visit is attributed a coding level. Emergency Department coding levels typically range from one to six, with level six indicating a critical patient. While in order to ensure as high a quality of care in the Emergency Department as possible it is crucial for visit documentation to be accurate and complete, often times it is difficult for a clinician to know whether or not the amount of documentation that has been completed is sufficient to attain an appropriate coding level in association with a patient's visit.

The issue is essentially two-fold. First, with the plethora of potential patient presentations and reasons for visits that exist in an Emergency Department, it is difficult for clinicians to maintain current knowledge of which presentations are to be coded at which coding levels. That is, it is difficult for clinicians to know what a so-called "typical" coding level (or "typical" visit level) should be for each patient presenting in the Emergency Department. Second, even if the clinician is aware of what a patient's "typical" visit level should be, it is difficult for the clinician to know if the elements that have been documented are sufficient to attain that level.

Coding meters exist in the marketplace today that allow a clinician or other individual to input information indicative of the quantity and nature of elements that have been documented in association with a patient visit. Subsequently, the coding meters output a visit or coding level in accordance with the CMS 95 Coding Guidelines which is supported by the documentation input. However, such coding meters can only offer an after-the-fact assessment whereby, if the documentation is insufficient to attain the appropriate coding level, the clinician must revisit the patient's chart and attempt to rectify the inconsistency. As such, this method is highly inefficient and presents ample opportunity for under-coding a patient visit.

Other solutions currently available in the marketplace offer a mechanism whereby the coding level may be checked prior to a clinician signing off on the patient's chart. However, this, too, is not a real-time solution the clinician may utilize at the time of documentation to ensure all appropriate measures are being taken to ensure the highest quality documentation. Thus, the step of having to check after-the-fact whether adequate documentation has been completed still must be performed.

Therefore, a system and method which offers clinicians a real-time view of a typical visit level associated with a reason for a patient's visit, as well as the E&M coding level associated with the current documentation would be desirable. Additionally, a system and method for identifying and indicating to a clinician, at the time the clinician is documenting a patient visit, those areas of documentation that are incomplete for achieving the appropriate E&M coding level would be advantageous.

BRIEF SUMMARY OF THE INVENTION

The present invention provides a method in a computing environment for professional evaluation and management (E&M) coding of a patient visit, e.g., to a hospital Emergency Department, based upon documentation. The method may include receiving a reason for the patient visit, determining a first numerical value representing a quantity of elements that have been documented in association with the patient visit, determining a current E&M coding level based upon the reason for the patient visit and the first numerical value, and determining a typical E&M coding level based upon the reason for the patient visit. Additionally, the method may include displaying a first view wherein the typical E&M coding level and the current E&M coding level are displayed in visual proximity with one another so that any discrepancy therebetween may be readily discernible.

If desired, the method may further include determining a second numerical value representing a quantity of elements that must be documented to achieve the typical E&M coding level associated with the reason for the patient visit and determining a difference between the second numerical value and the first numerical value, the difference representing the quantity of elements that remain to be documented to achieve the typical E&M coding level. Additionally, the method may include displaying a second view wherein one or more of the typical E&M coding level, the reason for the patient visit, the current E&M coding level, the first numerical value, the second numerical value, and the difference between the second numerical value and the first numerical value are displayed.

Still further, the method may include displaying a third view wherein a plurality of elements that are capable of being documented for E&M coding of the patient visit are displayed and, if desired, an indication of which the plurality of elements have already been documented.

In one embodiment, the method of the present invention provides updated information each time an additional element is documented in association with the patient visit. That is, the method may include receiving an additional documented element, determining a third numerical value representing an updated quantity of documented elements and determining an updated E&M coding level based upon the reason for the patient visit and the third numerical value.

Additionally, the method may include updating the first view such that the typical E&M coding level and the updated E&M coding level may be displayed in visual proximity with one another such that the difference therebetween may be readily discernible by a user. The second and third views may be similarly updated upon receipt of each additional documented element.

The present invention further provides a method for navigating to a portion of an electronic record, e.g., an electronic medical record, based upon E&M coding. The method may include displaying a plurality of elements that are capable of being documented for E&M coding, receiving user input indicative of one of the plurality of elements and, if content is present in the electronic record that is associated with the one of the plurality of elements, displaying the associated content. However, if no content is present in the electronic record that is associated with the one of the plurality of elements, the method may include displaying an indication that no associated content is present. In this instance, the method may further include displaying a user-selectable option to insert content into the electronic record wherein upon receiving user input indicating that content is to be inserted, the user is directed to that portion of the electronic record that is associated with the one of the plurality of elements so that content may be inserted. If desired, at least partially pre-established content may be inserted and subsequently personalized by the user.

Computer systems and computer-readable media having computer-executable instructions for performing the methods disclosed herein are also provided.

Additionally, the present invention provides a user interface embodied on at least one computer-readable medium for navigating to portions of an electronic record based upon E&M coding. The user interface may include a coding summary display area configured to display a typical E&M coding level based upon a reason for a patient visit and a current E&M coding level based upon a quantity of elements that have been documented in association with the patient visit. The method may further include a documentation summary display area configured to display one or more of the current E&M coding level, the quantity of documented elements, the quantity of elements that must be documented to achieve the typical E&M coding level, and the quantity of documents remaining to be documented to achieve the typical E&M coding level. Still further, the method may include a coding element display area configured to display a plurality of selectable element links each of which is indicative of an element that is capable of being documented for E&M coding, whereby following one of the selectable element links allows the user to navigate to content in the electronic record that is associated with the element indicated by that link.

BRIEF DESCRIPTION OF THE SEVERAL VIEWS OF THE DRAWING

The present invention is described in detail below with reference to the attached drawing figures, wherein:

FIG. 2 is an exemplary screen display illustrating a coding summary display area in accordance with an embodiment of the present invention;

FIG. 3 is an exemplary screen display illustrating a documentation summary display area in accordance with an embodiment of the present invention;

FIG. 4 is an exemplary screen display illustrating a coding element display area in accordance with an embodiment of the present invention;

FIG. 5 is an exemplary screen display indicating that the electronic record shown lacks documentation in association with the "cardiovascular" E&M coding element;

DETAILED DESCRIPTION OF THE INVENTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

The present invention provides computerized methods and systems for professional evaluation and management (E&M) coding of a patient visit based upon documentation. The present invention further provides computerized methods and systems for navigating to a portion of an electronic record, e.g., an electronic medical record, based upon E&M coding. An exemplary operating environment for the present invention is described below.

Figure 1:
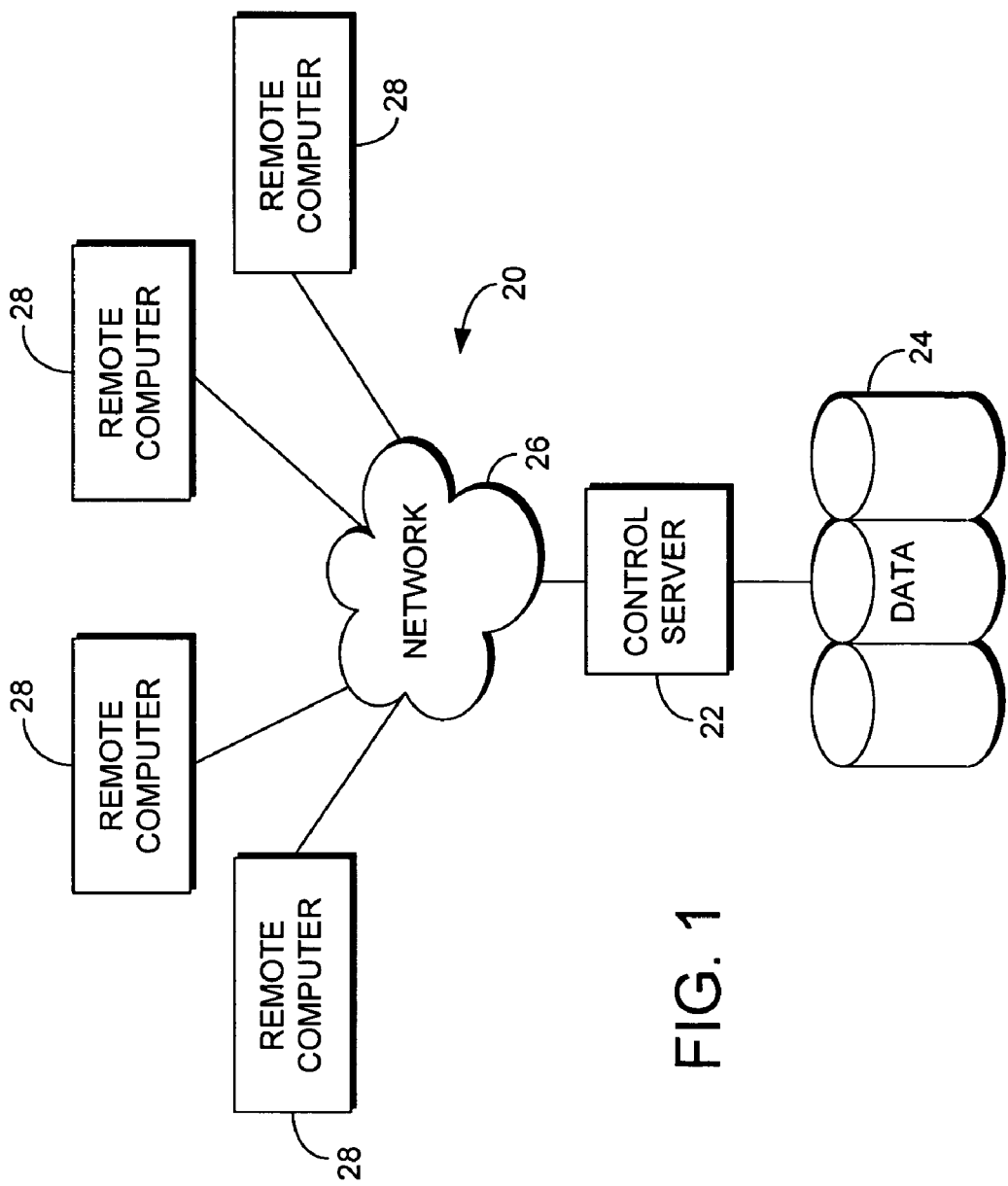
FIG. 1 is a block diagram of a computing system environment suitable for use in implementing the present invention.

Referring to the drawings in general, and initially to FIG. 1 in particular, an exemplary computing system environment, for instance, a medical information computing system, on which the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer readable media, for instance, database cluster 24. Computer readable media can be any available media that may be accessed by control server 22, and includes volatile and nonvolatile media, as well as removable and nonremovable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage or other magnetic storage device, or any other medium which can be used to store the desired information and which may be accessed by control server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for control server 22.

The control server 22 may operate in a computer network 26 using logical connections to one or more remote computers 28. Remote computers 28 may be located at a variety of locations in a medical environment, for example, but not limited to, clinical laboratories, hospitals and other inpatient settings, ambulatory settings, medical billing and financial offices, hospital administration settings, home health care environments, and clinicians' offices. Clinicians may include, but are not limited to, a treating physician or physicians, specialists such as surgeons, radiologists and cardiologists, emergency medical technicians, physicians' assistants, nurse practitioners, nurses, nurses' aides, pharmacists, dieticians, microbiologists, and the like. Remote computers 28 may also be physically located in non-traditional medical care environments so that the entire health care community may be capable of integration on the network. Remote computers 28 may be personal computers, servers, routers, network PCs, peer devices, other common network nodes, or the like, and may include some or all of the elements described above in relation to the control server 22.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in the control server 22, in the database cluster 24, or on any of the remote computers 28. For example, and not by way of limitation, various application programs may reside on the memory associated with any one or all of the remote computers 28. It will be appreciated by those of ordinary skill in the art that the network connections shown are exemplary and other means of establishing a communications link between the computers (e.g., control server 22 and remote computers 28) may be utilized.

In operation, a user may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. The control server 22 and/or remote computers 28 may include other peripheral output devices, such as speakers and a printer.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Figure 8:
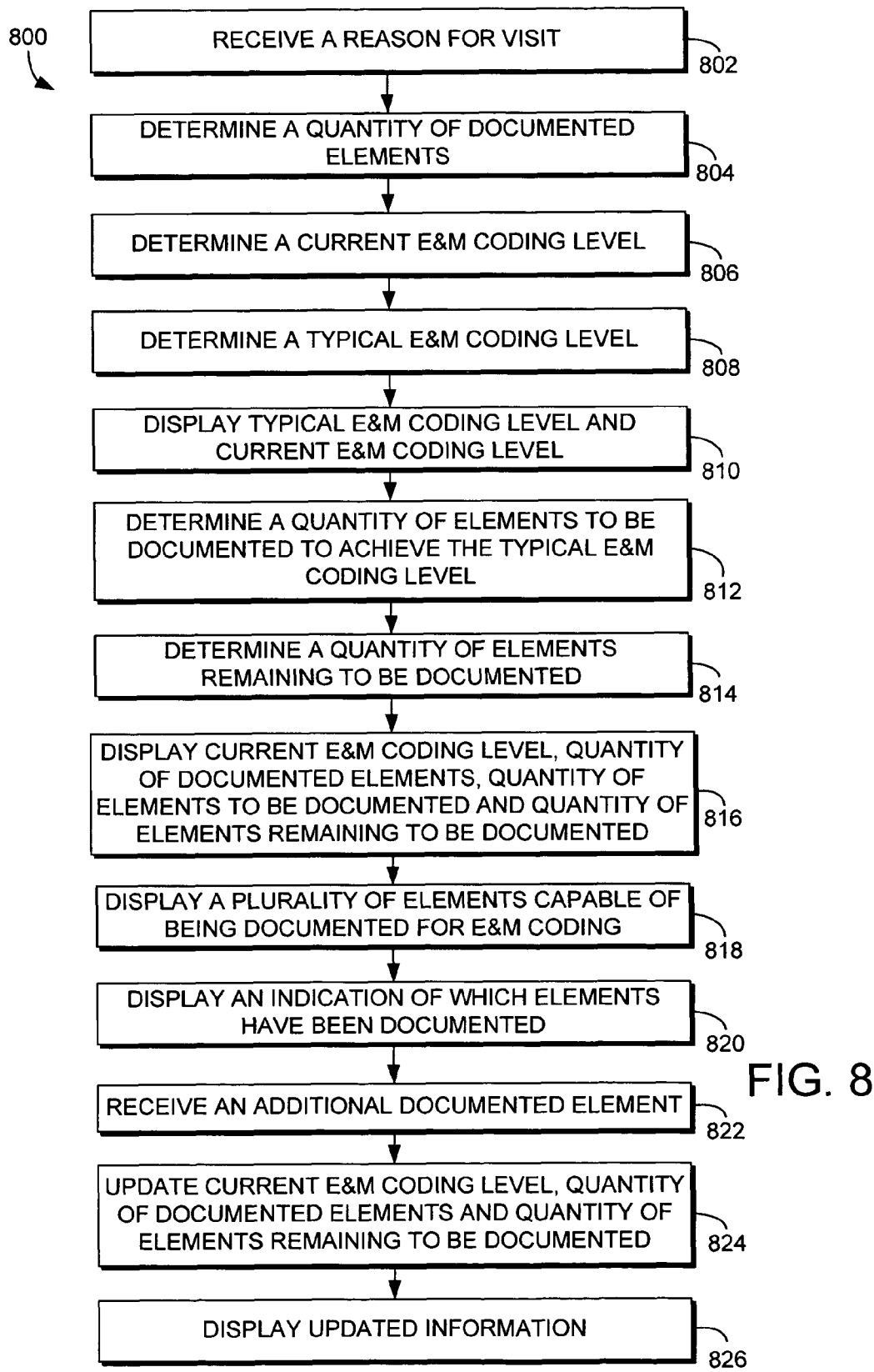
FIG. 8 is a flow chart representative of a computer program for E&M coding of a patient visit based upon documentation (i.e., documentation-based coding) in accordance with an embodiment of the present invention.

As previously mentioned, the present invention relates, in part, to a computerized method and system for professional evaluation and management (E&M) coding of a patient visit based upon documentation. With reference to FIG. 8, a flow chart representative of a method for such documentation-based coding in accordance with an embodiment of the present invention is illustrated and depicted generally as reference numeral 800. Method 800 may be implemented on the above-described exemplary computing system environment 20 (FIG. 1) and, by way of example only, may be utilized to aid a clinician in ensuring that documentation appropriate for a patient's clinical presentation and the reason for the patient's visit is completed. (The terms "individual", "person", and "patient" are used interchangeably herein and are not meant to limit the nature of the referenced individual in any way. Rather, the methods and systems described herein are equally applicable in, for instance, a veterinary setting. Further, use herein of the term "patient" is not meant to imply any particular relationship between the individual in question and those documenting the individual's visit.)

Initially, as shown at block 802, the system receives a reason for the patient's visit. For instance, if the patient presents to a hospital Emergency Department complaining of shortness of breath, an electronic record (e.g., and electronic medical record) of the patient's visit may be opened, e.g., using PowerNote ED available from Cerner Corporation of Kansas City, Mo. as described in U.S. Pat. No. 5,715,449 dated Feb. 3, 1998 and entitled "Method for Generating Structured Medical Text through User Selection of Displayed Text and Rules," and the reason for the patient's visit (e.g., dyspnea) may be input by a clinician or other authorized Emergency Department personnel. If the patient presents with multiple symptoms, that is, if there are multiple reasons for the patient's visit, all such reasons for the patient's visit will be input into the electronic record. This may either be done in a single electronic record or in a plurality of separate electronic records, each of which will be merged and associated with the patient's visit.

Subsequently, as shown at block 804, the system determines a quantity of elements (represented by a numerical value) that have been documented in association with the patient's visit. If documentation of the patient visit has just been initiated, the quantity of documented elements will likely be zero. However, if the electronic record is being accessed or viewed at an instance in time removed from the initial opening of the electronic record, elements may already be documented in association with the visit and the quantity of such elements will be determined.

Next, as shown at block 806, the system determines the current E&M coding level based upon the reason for the patient's visit and the quantity of documented elements. The current E&M coding level is calculated based upon the CMS 95 Coding Guidelines for Professional Evaluation and Management Coding. Subsequently or simultaneously, as shown at block 808, the system determines a so-called "typical" E&M coding level based upon the reason for the patient's visit. "Typical E&M coding level," as that term is used herein, refers to an average E&M coding level documented in association with the delineated reason for the patient's visit. These typical levels are standards that have been derived secondary to a review of several million patient charts in numerous hospitals and are intended to serve merely as a guideline for clinician's in documenting a patient visit.

In the event there are multiple reasons for the patient's visit, a typical visit level will be determined in association with each reason. However, for purposes of documentation, the reason for visit having the highest typical visit level will be utilized, as more fully described below.

Subsequently, as shown at block 810, the current E&M coding level and the typical E&M coding level may be displayed. It is currently preferred that the two values be displayed in visual proximity to one another so that any discrepancy therebetween may be easily discernible to the user. An exemplary screen display, depicted generally as reference numeral 100, illustrating this embodiment of the present invention is shown in FIG. 2.

Figure 2:
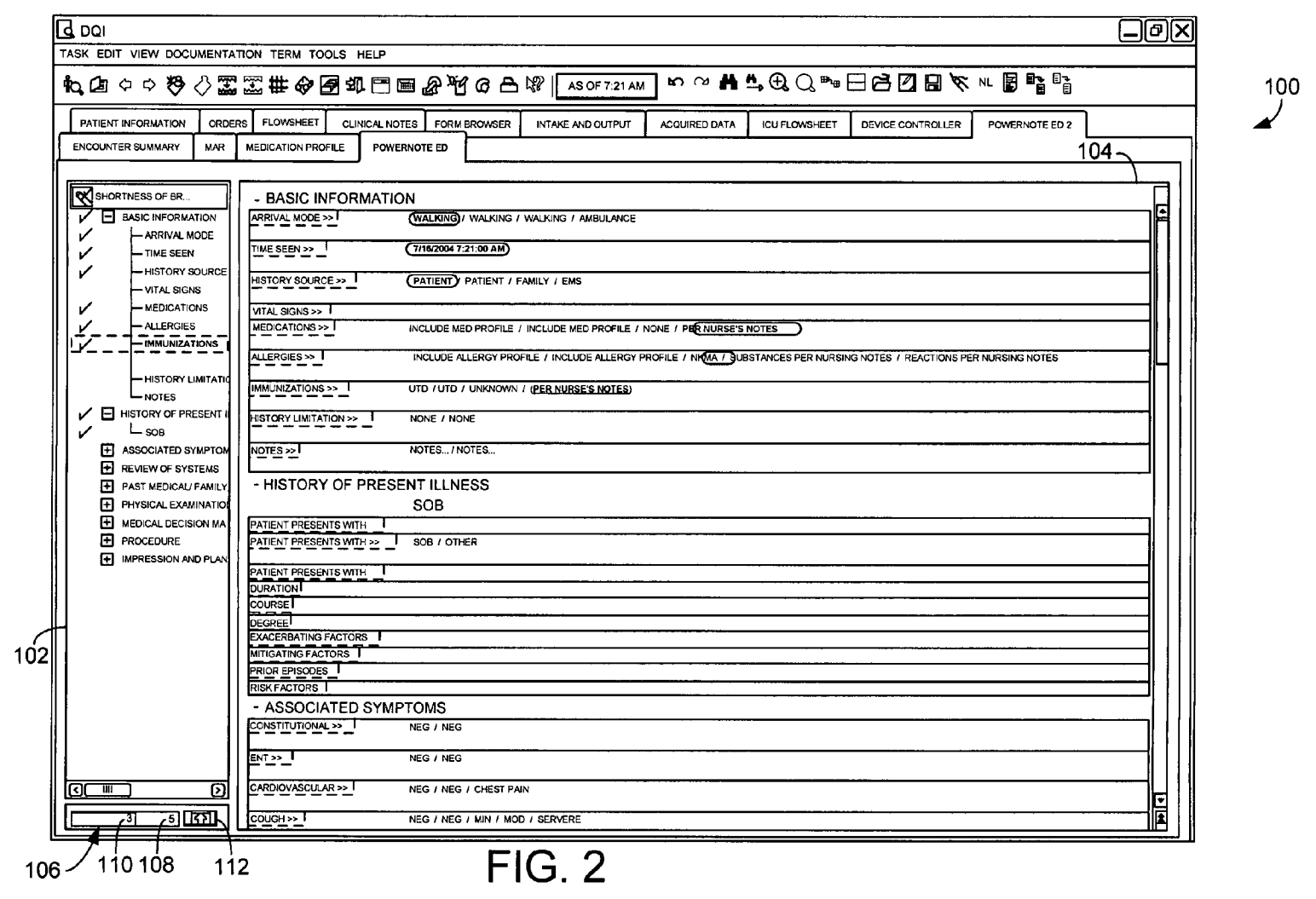

The screen display 100 of FIG. 2 includes a menu display area 102 and a documentation display area 104. The menu display area 102 illustrates, by way of example only, a description of the patient's clinical presentation (i.e., shortness of breath) and a menu in the form of a template-driven hierarchy showing various items that may be input as part of the patient's electronic record in association with the patient's visit. Template-driven hierarchical menus are known to those of ordinary skill in the art and, accordingly, are not further described herein. An exemplary structured documentation product utilizing such a template-driven hierarchical menu structure is the PowerNote ED available from the Cerner Corporation of Kansas City, Mo.

The documentation display area 104 of the screen display 100 illustrates the documentation that has been input with regard to the patient's visit. The view of the documentation display area 104 coincides with the view of the menu display area 102 to the extent possible in that the categories and subcategories shown in both display areas 102, 104 are the same. Some of these categories and subcategories (particularly those that are representative of components and/or subcomponents of the CMS 95 Coding Guidelines for Evaluation and Management Coding) are more fully described below.

The screen display 100 further includes a coding summary display area 106 configured to display the typical E&M coding level 108 based upon the reason for the patient's visit, the current E&M coding level 110 based upon the reason for the patient's visit, and the quantity of elements that have been documented in association therewith. In the screen display 100 of FIG. 2, the typical E&M coding level 108 and the current E&M coding level 110 are displayed in visual proximity to one another such that any discrepancy therebetween may be easily discernible. In the depicted instance, the typical visit level is indicated as a level 5 while the current documentation supports only a level 3 (i.e., the current E&M coding level 110 is 3). If the patient presented with multiple reasons for visit, the highest typical visit level associated is utilized.

It will be understood and appreciated by those of ordinary skill in the art that the typical E&M coding level, current E&M coding level, quantity of documented elements, and reason for patient's visit are exemplary in nature and are utilized herein merely for illustrative purposes.

The screen display 100 further includes a selectable view indicator 112. As the screen display 100 represented in FIG. 2 may be thought of as a "minimum view", the selectable view indicator 112 illustrates an arrow in only the upward-facing direction. In this instance, selection of the selectable view indicator 112 will provide the user with increased or more detailed information related to the coding of the patient visit, as more fully described below. In the currently preferred embodiment, the "minimum view" is the default view upon accessing and/or opening a patient's electronic record.

Referring back to FIG. 8, once the typical E&M coding level has been determined, the system determines the quantity of elements (represented by a numerical value) that are required to be documented to achieve the typical E&M coding level in accordance with the CMS 95 Coding Guidelines for Professional Evaluation and Management Coding. This is shown at block 812. The CMS 95 Coding Guidelines for Professional Evaluation and Management Coding break down element documentation into a number of components and subcomponents. For instance, the three primary components in establishing an E&M coding level are History (HX), Examination (EX), and Medical Decision Making (MDM).

History may be further divided into three subcomponents: History of Present Illness (HPI), Review of Symptoms (ROS), and Past, Family, and Social History (PFS). There are a number of elements within each component/subcomponent grouping which may be documented in association with a patient's visit. For instance, the elements that may be documented with regard to HPI include duration, timing, location, quality, severity, associated symptoms (AOS), modifying factors, and context. The elements that may be documented with regard to ROS include constitutional, eyes, ENMT, cardiovascular, respiratory, gastrointestinal, genitourinary, musculoskeletal, integumentary, neurological, psychiatric, endocrine, hema/lymph, and allergic/immuno. The elements that may be documented with regard to PFS include past, family, and social history. The elements that may be documented with regard to Examination include constitutional, eyes, ENMT, cardiovascular, respiratory, gastrointestinal, genitourinary, musculoskeletal, integumentary, neurological, psychiatric, endocrine, and hema/lymph/immuno. In a currently preferred embodiment of the invention, the quantity of elements to be documented to achieve the typical E&M coding level is determined by the system based upon these components and subcomponents rather than the documentation as a whole. In this embodiment, the quantity of documented elements determined at block 804 is also determined based upon components and subcomponents.

Subsequently, as shown at block 814, the system determines a quantity of elements remaining to be documented to achieve the typical E&M coding level for the patient's visit by determining the difference between the quantity of elements to be documented and the quantity of elements that have been documented. Again, in the currently preferred embodiment, this is performed on the basis of components and subcomponents rather than on the documentation as a whole.

Next, as shown at block 816, the current E&M coding level, the quantity of documented elements, the quantity of elements to be documented and the quantity of elements remaining to be documented may be displayed. An exemplary screen display, depicted generally as reference numeral 100a, illustrating this embodiment of the present invention is shown in FIG. 3.

Figure 3:
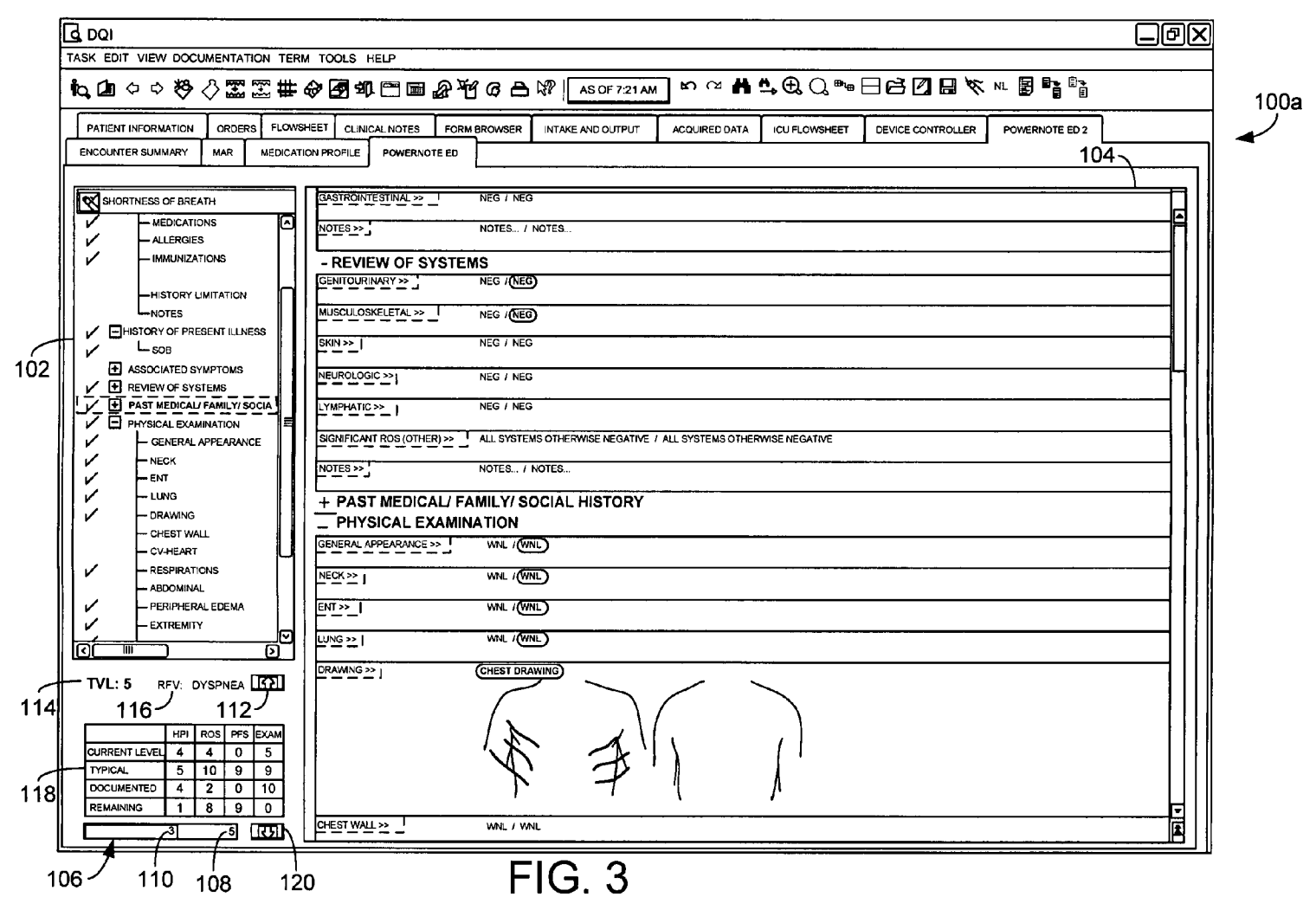

The screen display 100a of FIG. 3 is similar to the screen display 100 of FIG. 2 except that it includes additional information related to coding of the patient's visit. In this regard, the screen display 100a includes a menu display area 102 (albeit relatively more compact than the similar menu display area 102 of screen display 100) and a documentation display area 104. The screen display 100a additionally includes the coding summary display area 106, typical E&M coding level 108 and current E&M coding level 110, as were also shown in screen display 100. However, the screen display 100a further includes a documentation summary display area 118 wherein additional information related to the coding of the patient's visit may be displayed.

In this regard, the documentation summary display area 118 includes, by way of example only and not limitation, a grid-like presentation of the CMS 95 Coding Guidelines History subcomponents HPI, ROS and PFS, as well as the Examination component and indicates the current E&M coding level, the typical quantity of documented elements necessary to achieve the typical E&M coding level for the patient's visit, the quantity of documented elements, and the quantity of elements remaining to be documented with regard to each component/subcomponent.

There are a couple of items concerning documentation summary display area 118 that are worthy of note. First, while the CMS 95 Coding Guidelines for Professional Evaluation and Management Coding specify a separate component for Medical Decision Making with regard to determination of coding level, such a category is absent from the documentation display area 118 of screen display 100a. It will be understood and appreciated by those of ordinary skill in the art, however, that such category may be added and the associated coding information determined, if desired. Second, the current E&M coding level for each of the components/subcomponents are different than the overall current E&M coding level 110 shown in the coding summary display area 106. This is because the overall current E&M coding level 110 represents an aggregate figure which takes into account the relevant information for each of the individual components/subcomponents.

The screen display 100a of FIG. 3 additionally includes a "TVL" display area 114 where the typical visit level based upon the reason for the patient's visit may be more prominently displayed and a "RFV" display area 116 where the reason for the patient's visit may be displayed. In the screen display 100a of FIG. 3, the TVL display area indicates a typical visit level of 5, consistent with that indicated by the typical E&M coding level 108 displayed in the coding summary display area 106, and the RFV display area indicates a reason for visit of "dyspnea," consistent with the description of the patient's clinical presentation of "shortness of breath" shown at the top of the menu display area 102. If there are multiple reasons for the patient's visit, the TVL display area 114 illustrates the highest typical E&M coding level associated with any of the reasons for the patient's visit. Similarly, the values in the grid-like presentation of the documentation summary display area 118 include values indicative of the documentation necessary for achieving the highest associated typical E&M coding level. The RFV display area 116 may show either only the reason for visit corresponding to the highest typical E&M coding level, or may show all reasons for the patient's visit.

It will be understood and appreciated by those of ordinary skill in the art that the values in the grid-like presentation of the documentation summary display area 118 are exemplary in nature and are presented herein for illustrative purposes only, particularly, those values indicating a typical quantity of documents necessary to achieve a particular typical E&M coding level.

The screen display 100a further includes a selectable view indicator 112 having an upward-facing arrow depicted thereon indicating that selection thereof will provide the user with additional information regarding the coding of the patient's visit. Additionally, the screen display 100a includes a second selectable view indicator 120 having a downward-facing arrow depicted thereon indicating that selection thereof will provide the user with less information regarding the coding of the patient's visit than the current view. Selection of the second selectable view indicator 120 of screen display 100a will return the user to the minimum view screen display 100 shown in FIG. 2. As either more or less information regarding the coding of the patient's visit may be attained from this view, screen display 100a may be referred to as a "moderate view." As more fully described below, the "moderate view" shown in screen display 100a may serve as a navigator to a "full view" shown in the screen display 100b of FIG. 4.

Examination of the documentation summary display area 118 of screen display 100a illustrates, by way of example only, that with respect to the HPI subcomponent, a current E&M coding level of four has been achieved. Typically, five elements are documented for the HPI subcomponent when a patient presents with dyspnea, four elements have been documented within the HPI subcomponent and documentation of one additional document within this subcomponent is necessary to achieve the typical E&M coding level shown in the TVL display area 114. Similarly, the screen display 100a illustrates that, with respect to the ROS subcomponent, a current E&M coding level of four has been achieved. Typically, ten elements are documented for the ROS subcomponent when a patient presents with dyspnea, two elements have been documented within the ROS subcomponent and documentation of eight additional elements within this subcomponent are necessary to achieve the typical E&M visit level shown in the TVL display area 114. With respect to the PFS subcomponent, the screen display 100a illustrates that a current E&M coding level of zero has been achieved. Typically, nine elements are documented for the PFS subcomponent when a patient presents with dyspnea, zero elements have been documented within the PFS subcomponent and documentation of nine additional elements within this subcomponent are necessary to achieve the typical E&M visit level shown in the TVL display area 114. With respect to the Examination component, the screen display 100a illustrates that a current E&M coding level of five has been achieved. Typically, nine elements are documented for the Examination component when a patient presents with dyspnea, ten elements have been documented within the Examination component and, accordingly, no additional documentation is necessary for this component to achieve the typical E&M visit level shown in the TVL display area 114.

Referring back to FIG. 8, if desired, the system may display a plurality of elements capable of being documented for E&M coding, as shown at block 818. An exemplary screen display, depicted generally as reference numeral 100b, in accordance with this embodiment is shown in FIG. 4.

Figure 4:
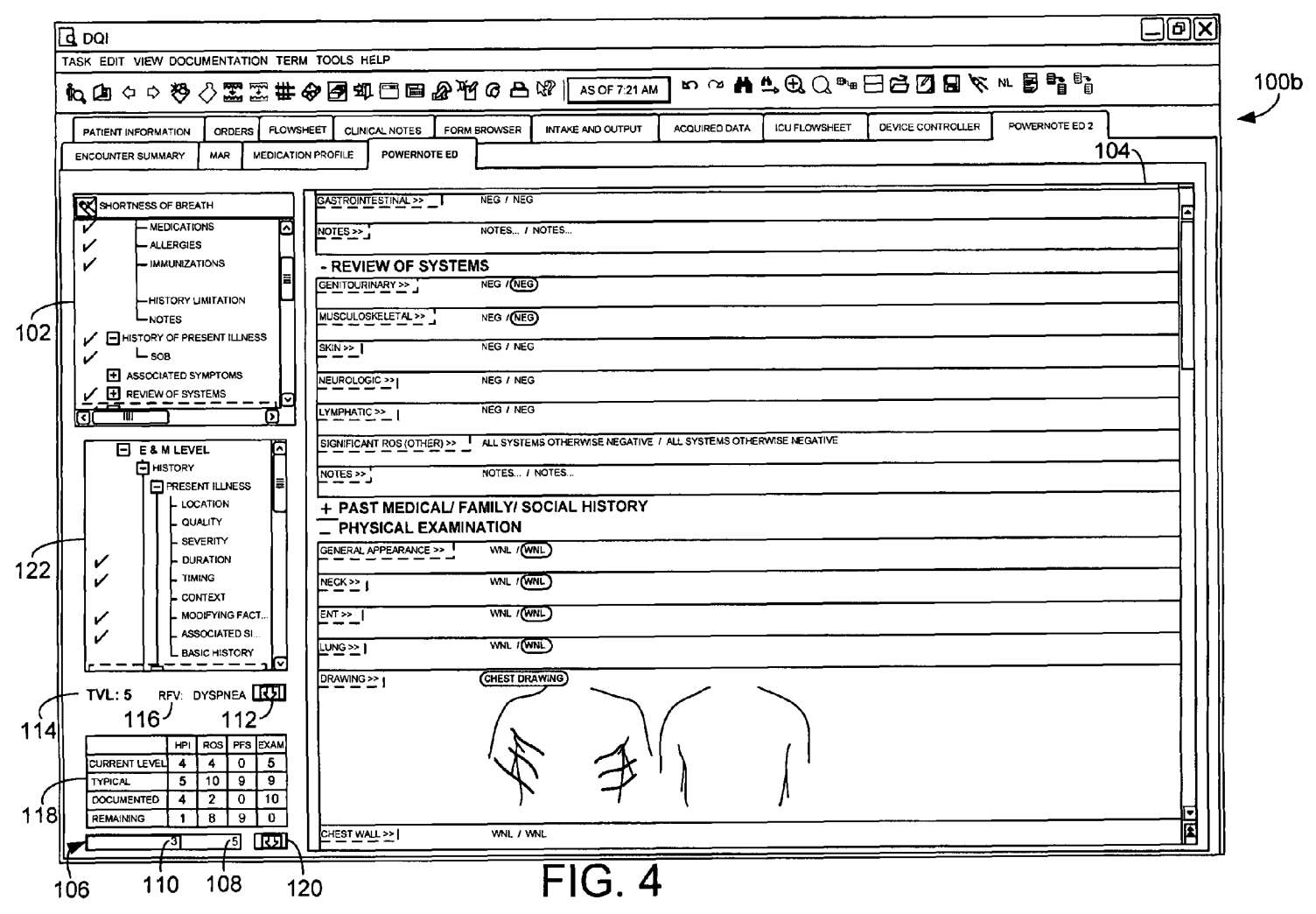

The screen display 100b of FIG. 4 is similar to the screen display 100a of FIG. 3 except that it includes additional information related to coding of the patient's visit. In this regard, the screen display 100b includes a menu display area 102 (albeit relatively more compact than the similar menu display area 102 of screen display 100a) and a documentation display area 104. Screen display 100b additionally includes the coding summary display area 106, typical E&M coding level 108 and current E&M coding level 110, as were also shown in screen display 100a. Further, screen display 100b includes a documentation summary display area 118, TVL display area 114 and RFV display area 116, as were shown in screen display 100a. However, the screen display 100b further includes a coding element display area 122 wherein additional information related to the coding of the patient's visit may be displayed.

In this regard, the coding element display area 122 includes, by way of example only and not limitation, a template-driven hierarchical structure having the elements within the components and subcomponents hereinabove described that are set forth in the CMS 95 Guidelines for Evaluation and Management Coding visible to the user. User selection of the selectable view indicator 112 of FIG. 3 or of any of the values within the grid-like structure of the documentation summary display area 118 will expand the view to the screen display 100b shown in FIG. 4.

Referring back to FIG. 8, if desired, the system may further display an indication of which elements within each of the components and subcomponents has been documented. This is shown at block 820. With reference to the screen display 100b of FIG. 4, such indication (by way of example only) is a check-mark shown to the left of the indicated element in the hierarchical tree structure of the coding element display area 122.

By way of example, the coding element display area 122 illustrates a hierarchical listing of elements that may be documented within the HPI subcomponent and illustrates that four of such elements (duration, timing, modifying factors and associated symptoms) have been documented. This is consistent with the documentation summary display area 118 which indicates that four elements have been documented with respect to the HPI subcomponent. As one more element within the HPI subcomponent is necessary to be documented to achieve the typical visit level associated with the patient's dyspnea presentation, the clinician (or other qualified individual) may select which of location, quality, severity, context and basic history to document.

It should be noted that both the selectable view indicator 112 and the second selectable view indicator 120 of screen display 100b depict downward-facing arrows. This is indicative of the fact that the view shown is the most detailed view with respect to coding information that the system is capable of showing. Accordingly, screen display 100b may be thought of as a "full view." Selection of either the selectable view indicator 112 or the second selectable view indicator 120 will return the user to screen display 100a as shown in FIG. 3.

The current E&M coding level 110 of the coding summary display area 106 of FIGS. 2, 3, and 4 as well as the current E&M coding level, the quantity of documented elements and the remaining quantity of elements to be documented shown in the documentation summary display area 118 of FIGS. 3 and 4 are dynamic. That is, each shall increment and/or decrement as necessary when elements associated with the appropriate component/subcomponent are completed or cleared from the electronic record, respectively. Accordingly, referring back to FIG. 8, if an additional documented element is received, as indicated at block 822, the system will update the current E&M coding level (if appropriate), as well as the quantity of documented elements and the quantity of elements remaining to be documented. This is shown at block 824. This updated information will then be displayed in the coding summary display area 106 of FIGS. 2, 3, and 4 and in the documentation summary display area 118 of FIGS. 3 and 4. This updated displaying of information is shown at block 826 of FIG. 8.

By way of example only, if an additional element of the HPI subcomponent were to be documented by the clinician, the number of documented elements shown in the documentation summary display area 118 under the heading of "HPI" of FIGS. 3 and 4 would be modified from four to five and the number of documents remaining to be documented would be modified from one to zero. Additionally, if appropriate, the current E&M coding level indicated in the documentation summary display area 118 under the heading of "HPI" would be modified, as would the overall current E&M coding level 110 shown in the coding summary display area 106 of FIGS. 2, 3, and 4.

In one embodiment, if the current overall E&M level 110 shown in the coding summary display area 106 exceeds the typical E&M coding level 108 associated with the reason for the patient's visit, a visual and/or audio alert may be provided to alert the clinician that inaccurate visit documentation may exist.

Figure 9:
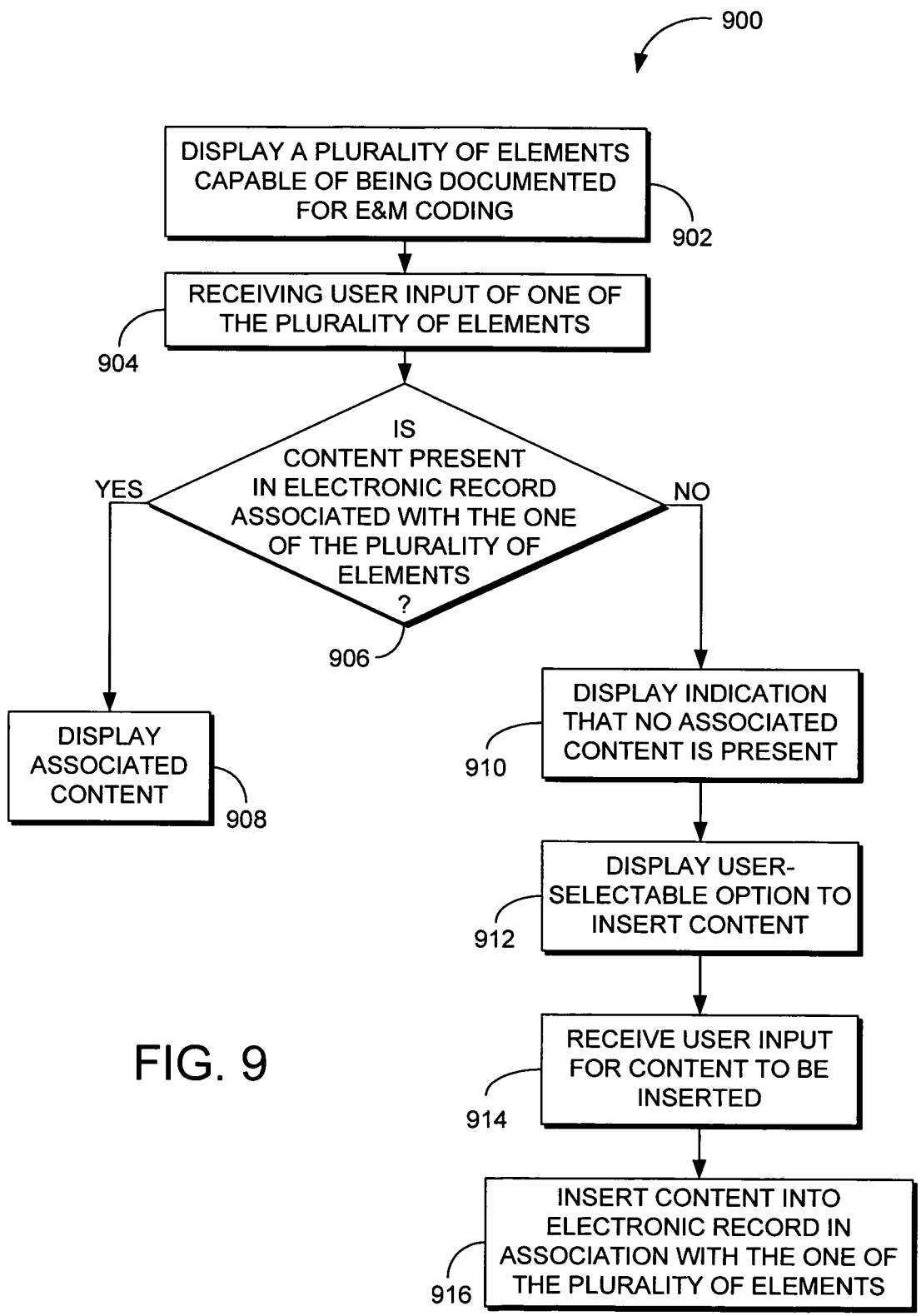
FIG. 9 is a flow chart representative of a computer program for navigating to a portion of an electronic record based upon E&M coding (i.e., coding-based document navigation) in accordance with an embodiment of the present invention.

The present invention further relates to a computerized method and system for navigating to a portion of an electronic record, e.g., an electronic medical record, based upon professional evaluation and management (E&M) coding. With reference to FIG. 9, a flow chart representative of such coding-based document navigation in accordance with an embodiment of the present invention is illustrated and depicted generally as reference numeral 900. Method 900 maybe implemented on the above-described exemplary computing system environment 20 (FIG. 1) and, by way of example only, may be utilized to aid a clinician in documenting elements in a patient's electronic record that are appropriate for the patient's clinical presentation and the reason for the patient's visit.

Figure 5:
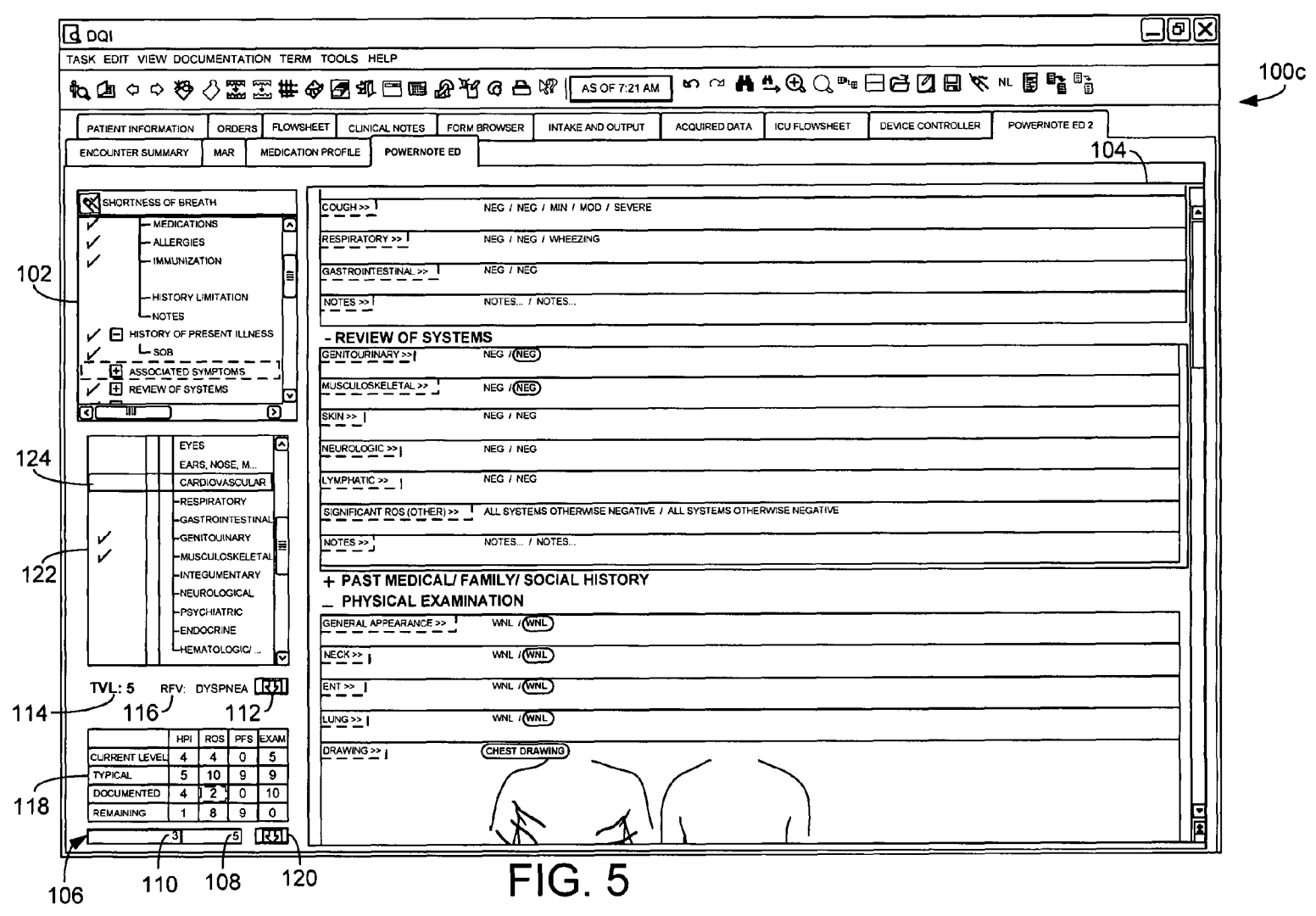

Initially, as shown at block 902, the system displays a plurality of elements that are capable of being documented for E&M coding. An exemplary screen display, depicted generally as reference numeral 100c, in accordance with this embodiment of the present invention is shown in FIG. 5. The screen display 100c of FIG. 5 is similar to the screen display 100b of FIG. 4 with a couple of notable exceptions. First, note that in the documentation summary display area 118 under the heading "ROS," a dashed-line box appears around the number of items that have been documented. This is indicative of the user's selection of this particular box within the grid and is intended to illustrate the fact that such box represents a selectable link. More generally, each of the grid boxes representing the number of documented elements represents a selectable link, selection of which causes the coding element display area 122 to display a hierarchical tree structure representing those elements that may be documented under the particular component/subcomponent, as well as an indication of which elements associated with the component/subcomponent have been documented. In this instance, selection of the grid box for documented elements under the heading "ROS" results in the elements that may be documented under the "Review of Systems" subcomponent being displayed in the coding element display area 122. Further, the coding element display area 122 indicates (by check-marks to the left thereof) that the genitourinary and musculoskeletal elements have already been documented, consistent with the indication in the selected grid box that two elements have been documented.

Further note that a box appears around the "cardiovascular" subcomponent 124 in the coding element display area 122 of the screen display 100c. This is intended to illustrate that each of the elements set forth in the coding element display area 122 represents a selectable link, selection of which navigates the user to any content in the electronic record associated therewith, as more fully described below.

Returning to FIG. 9, once the plurality of elements capable of being documented for E&M coding has been displayed, the system receives user input selecting one of the displayed elements. This is shown at block 904. In the above-described example relating to FIG. 5, the user has selected the "cardiovascular" element within the subcomponent "Review of Systems."

Next, as shown at block 906, the system determines whether or not any content is present in the electronic record that is associated with the selected element. If there is associated content, such content is displayed, as shown at block 908. Typically, display of the associated content would result in a re-orientation of the view in the documentation display area 104 (FIG. 5) such that the selected content is centered within the documentation display area 104 itself.

If, however, no content is present in the electronic record that is associated with the selected element, the system displays an indication that no such associated content is present. This is shown at block 910 of FIG. 9. Subsequently, a user-selectable option to insert content in association with the selected element is displayed, as shown at block 912. If the system then receives user input indicating that content is to be inserted which may be, e.g., specific to the patient's reason for visit, into the electronic record, as shown at block 914, the user will be directed to that portion of the electronic record that is associated with the selected elements so that content may be inserted. This is shown at block 916. If desired, at least partially pre-established content may be inserted and subsequently personalized by the user, as more fully described below.

Figure 6:
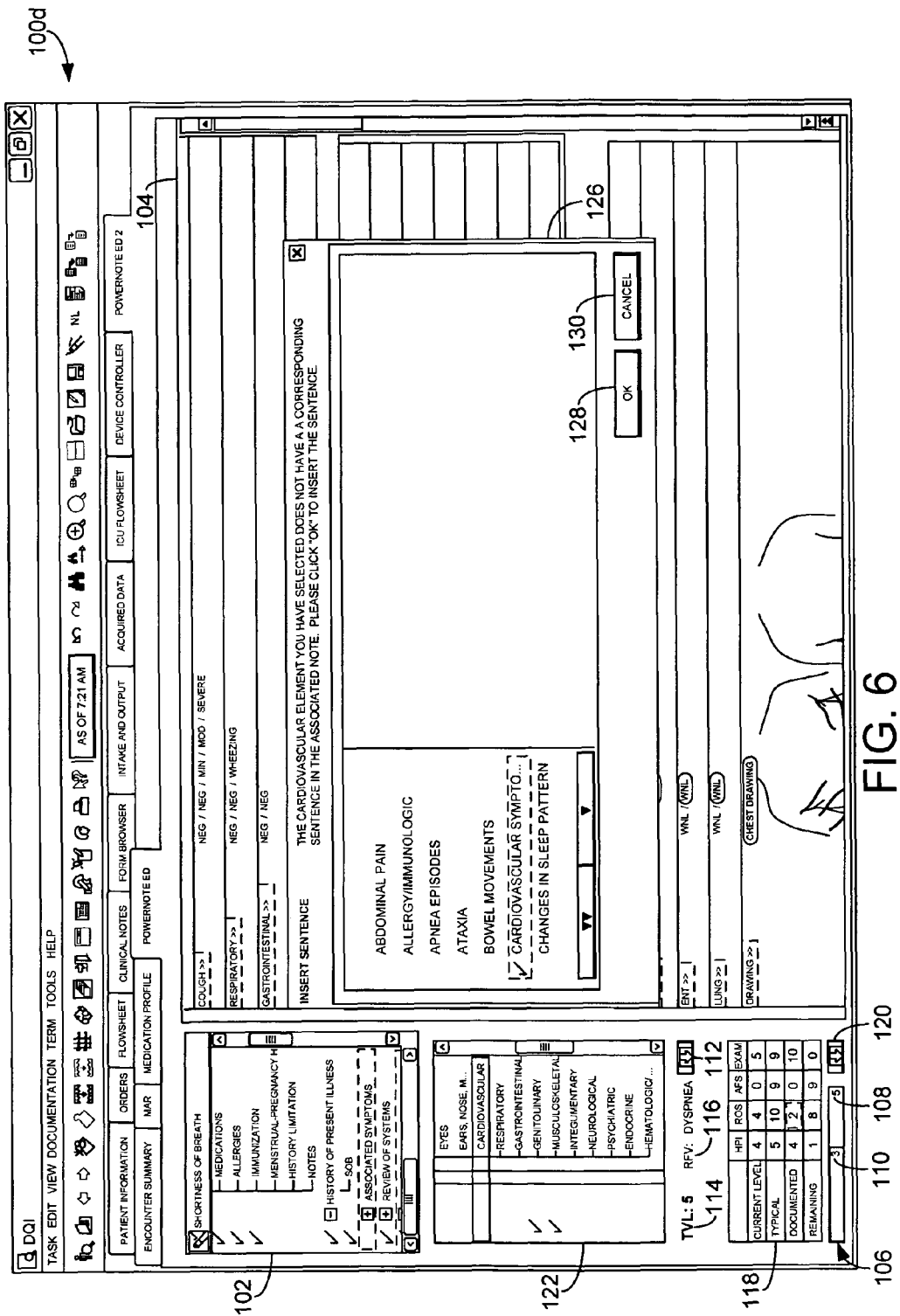
FIG. 6 is an exemplary screen display illustrating a user-selectable option for insertion of content into the electronic record to be associated with the "cardiovascular" E&M coding element.
Figure 7:
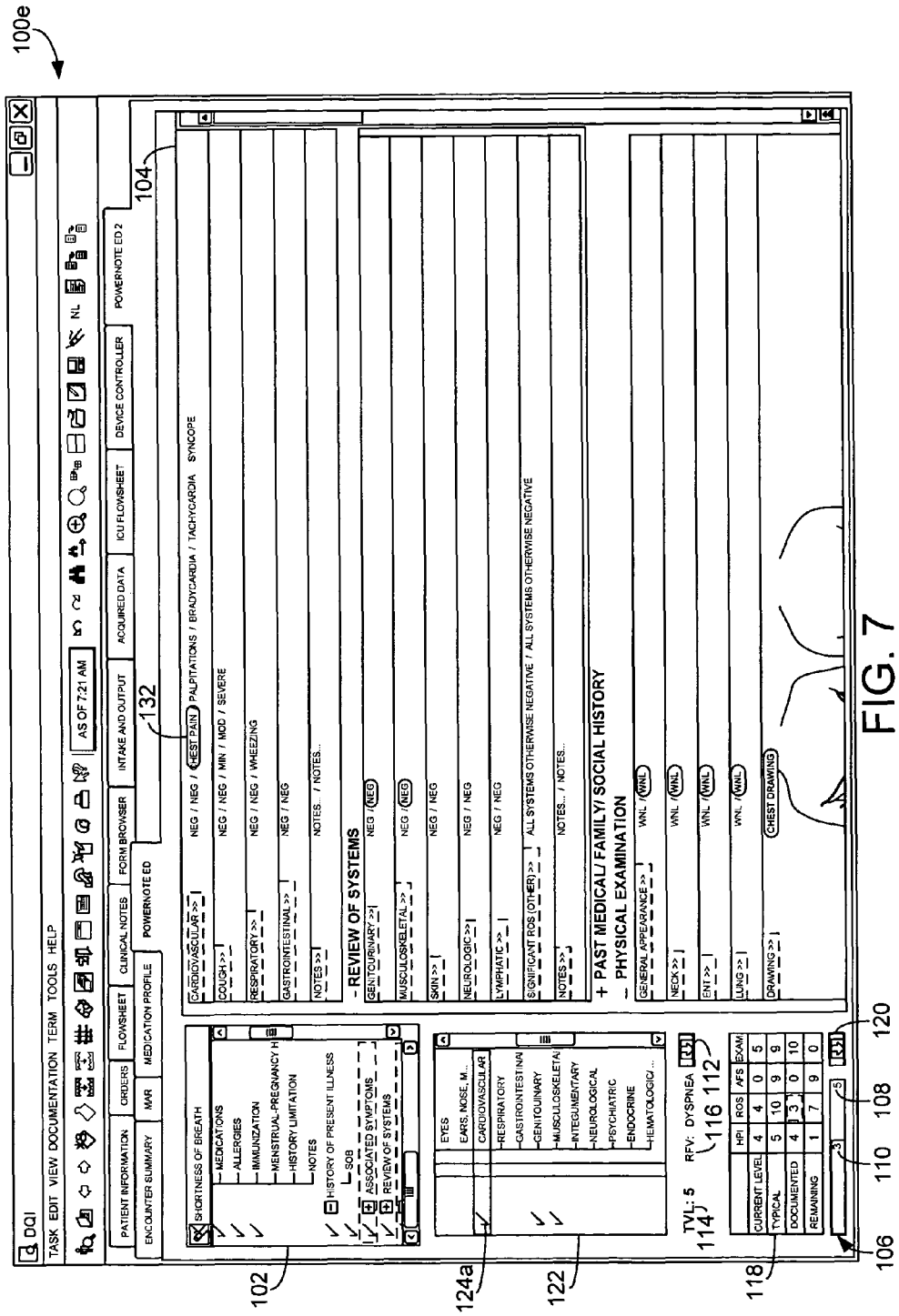
FIG. 7 is an exemplary screen display illustrating insertion of the at least partially pre-established content into the electronic record and concurrent indication that documentation is now associated with the "cardiovascular" E&M coding element in the electronic record.

Referring to FIG. 6, an exemplary screen display, depicted generally as reference numeral 100d, is shown. The screen display 100d is similar to the screen display 100c of FIG. 5 but further includes a content insertion window 126 that indicates that no content is present in the electronic record in association with the cardiovascular element and provides the user with a selectable option to insert content into the electronic record. If the user selects the "cancel" indicator 130, no content will be entered into the record. However, if the user selects the "ok" indicator 128, the content insertion window 126 will close and the user will be directed to that portion of the electronic record associated with the cardiovascular element so that content may be inserted in association therewith. If desired, at least partially pre-established content may be inserted which may be, e.g., specific to the patient's reason for visit, and subsequently personalized by the user. This is shown in the exemplary screen display of FIG. 7 depicted generally as reference numeral 100e.

In the illustrated embodiment, at least partially pre-established content was inserted in association with the cardiovascular element and is shown in the top line of the documentation display area 104 following the "cardiovascular>>" indicator of screen display 100e. The documentation display area 104 also indicates that the clinician (or other qualified personnel) has personalized the pre-established content by indicating at 132 that the patient presented with chest pain. This personalization may be done directly in the documentation display area 104 once the partially pre-established content has been entered.

Note that as content has now been entered in association with the cardiovascular element, an indicator 124a is shown (as a check-mark to the left thereof) in association with the element in the hierarchical tree structure of the coding element display area 122. Additionally, the quantity of documented elements and the documents remaining to be documented with regard to the "ROS" subcomponent have been updated to three and seven, respectively, in the documentation summary display area 118.

In summary, the present invention provides computerized methods and systems for professional evaluation and management coding of a patient visit based upon documentation. Such methods and systems increase efficiency and enhance the quality of clinician documentation by permitting automatic coding as a byproduct of documentation and eliminating the necessity for an after-the-fact check of the patient's chart to ensure appropriate documentation. The present invention further provides computerized methods and systems for navigating to a portion of an electronic record, e.g., an electronic medical record, based upon professional evaluation and management coding, as well as the automatic insertion of document content where necessary, thus increasing the efficiency of clinician documentation.

Although the invention has been described with reference to the preferred embodiments illustrated in the attached drawing figures, it is noted that substitutions may be made and equivalents employed herein without departing from the scope of the invention recited in the claims. For instance, additional steps may be added and steps may be omitted without departing from the scope of the invention.

The invention claimed is:

1. One or more computer-storage media having instructions embodied thereon for performing a method for navigating to a portion of an electronic record based upon coding, the method comprising:
receiving an input identifying a reason for a patient visit;
based on the reason for the patient visit, identifying a plurality of evaluation and management (E&M) coding components, wherein each E&M coding component includes a plurality of elements for E&M coding;
displaying each E&M coding component, wherein each E&M coding component is associated with:
(i) a first numerical value representing a quantity of elements associated with the E&M coding component that have been documented in a patient's electronic record, wherein the first numerical value is used to determine a current E&M coding level; and
(ii) a second numerical value representing a quantity of undocumented elements associated with the E&M coding component that remain undocumented in the patient's electronic record and are required to achieve a typical E&M coding level, wherein the typical E&M coding level is based on the reason for the patient visit;
receiving a user selection of a selectable indicator associated with one of the first numerical value, the second numerical value, the current E&M coding level, or the typical E&M coding level, wherein each of the first numerical value, the second numerical value, the current E&M coding level, and the typical E&M coding level are associated with one of the E&M coding components;
in response to receiving the selection of the selectable indicator, displaying the plurality of elements for E&M coding associated with the E&M coding component indicated by the selectable indicator, wherein the displayed plurality of elements for E&M coding includes both elements that have been documented in the patient's electronic record and elements that have not been documented in the patient's electronic record;
receiving a second user selection of one of the plurality of elements;
referencing a data store that includes the portion of the patient's electronic record;
determining if content is present in the patient's electronic record that is associated with the selected one of the plurality of elements; and
incident to determining that associated content is present in the patient's electronic record, simultaneously displaying the associated content in the patient's electronic record, each of the plurality of elements for E&M coding a patient visit, and the selected one of the plurality of elements corresponding with the associated content, wherein the selected one of the plurality of elements corresponding with the associated content is associated with a completion indicator indicating that the element has been documented in the patient's electronic record.

2. The media of claim 1, wherein if it is determined that no content is present in the electronic record that is associated with the one of the plurality of elements, the method further comprises displaying an indication that no associated content is present.

3. The media of claim 1, wherein if it is determined that no content is present in the electronic record that is associated with the one of the plurality of elements, the method further comprises displaying a user-selectable option to insert content into the electronic record.

4. The media of claim 3, further comprising:
receiving user input indicating content is to be inserted into the electronic record; and
directing the user to the portion of an electronic record associated with the one of the plurality of elements so that content may be inserted.

5. The media of claim 4, further comprising inserting content into the portion of the electronic record associated with the one of the plurality of elements and storing the inserted content in the data store in association with the portion of the electronic record.

6. The media of claim 5, wherein the content inserted into the portion of the electronic record associated with the one of the plurality of elements includes a portion which is at least partially pre-established.

7. The media of claim 6, further comprising receiving user input indicative of personalization of the portion of the content which is at least partially pre-established.

8. A computer system embodied on one or more computer storage media having computer-executable instructions embodied thereon for navigating to a portion of an electronic record based upon coding, the computer system comprising:
a first receiving module for receiving an input identifying a reason for a patient visit;
an identifying module for identifying a plurality of evaluation and management (E&M) coding components, wherein each E&M coding component includes a plurality of elements for E&M coding;
a first display module for displaying each E&M coding component, wherein each E&M coding component is associated with:
(i) a first numerical value representing a quantity of elements associated with the E&M coding component that have been documented a patient's electronic record, wherein the first numerical value is used to determine a current E&M coding level; and
(ii) a second numerical value representing a quantity of undocumented elements associated with the E&M coding component that remain undocumented in the patient's electronic record and are required to achieve a typical E&M coding level, wherein the typical E&M coding level is based on the reason for the patient visit; and
a second receiving module for receiving a user selection of a selectable indicator associated with one of the first numerical value, the second numerical value, the current E&M coding level, or the typical E&M coding level, wherein each of the first numerical value, the second numerical value, the current E&M coding level, and the typical E&M coding level are associated with one of the E&M coding components;
a second display module for displaying the plurality of elements for E&M coding associated with the E&M coding component indicated by the selectable indicator, wherein the displayed plurality of elements for E&M coding includes both elements that have been documented in the patient's electronic record and elements that have not been documented in the patient's electronic record;
a third receiving module for receiving a user selection of one of the plurality of elements; and
if content is present in the patient's electronic record that is associated with the one of the plurality of elements, a third display module for simultaneously displaying the associated content, each of the plurality of elements for E&M coding a patient visit, and the one of the plurality of elements corresponding to the associated content, wherein the one of the plurality of elements corresponding to the associated content is associated with a completion indicator indicating that the one of the plurality of elements has been documented in the patient's electronic record.

9. The computer system of claim 8, wherein if no content is present in the electronic record that is associated with the one of the plurality of elements, the computer system further comprises a fourth display module for displaying an indication that no associated content is present.

10. The computer system of claim 8, wherein if no content is present in the electronic record that is associated with the one of the plurality of elements, a fifth display module for displaying a user-selectable option to insert content into the electronic record.

11. The computer system of claim 10, further comprising:
   a fourth receiving module for receiving user input indicating content is to be inserted into the electronic record; and
   a directing module for directing the user to a portion of the electronic record associated with the one of the plurality of elements so that content may be inserted.

12. The computer system of claim 11, further comprising an insertion module for inserting content into the portion of the electronic record associated with the one of the plurality of elements.

13. The computer system of claim 12, wherein the content inserted into the portion of the electronic record associated with the one of the plurality of elements includes a portion which is at least partially pre-established.

14. The computer system of claim 13, further comprising a fifth receiving module for receiving user input indicative of personalization of the portion of the content which is at least partially pre-established.

* * * * *